US010711025B2

(12) United States Patent
López Cremades

(10) Patent No.: US 10,711,025 B2
(45) Date of Patent: *Jul. 14, 2020

(54) PROCESS FOR THE PREPARATION OF DIOSMIN

(71) Applicant: INTERQUIM, S.A., Sant Cugat del Vallès (Barcelona) (ES)

(72) Inventor: Francisco Javier López Cremades, Beniel-Murcia (ES)

(73) Assignee: INTERQUIM, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,118

(22) Filed: Apr. 2, 2019

(65) Prior Publication Data
US 2019/0225639 A1 Jul. 25, 2019

Related U.S. Application Data

(63) Continuation of application No. 15/544,174, filed as application No. PCT/EP2016/052165 on Feb. 2, 2016, now Pat. No. 10,287,310.

(30) Foreign Application Priority Data

Feb. 3, 2015 (EP) .................................... 15153537

(51) Int. Cl.
*C07H 17/07* (2006.01)
*C07H 1/00* (2006.01)

(52) U.S. Cl.
CPC ............... *C07H 17/07* (2013.01); *C07H 1/00* (2013.01)

(58) Field of Classification Search
None
See application file for complete search history.

(56) References Cited

U.S. PATENT DOCUMENTS 4,078,137 A 3/1978 Schmid et al.

FOREIGN PATENT DOCUMENTS

| BE | 904614 A1 | 8/1986 |
| DE | 2602314 A1 | 11/1976 |
| DE | 2740950 A1 | 3/1979 |
| EP | 0 900 582 A1 | 3/1999 |
| ES | 440427 A1 | 3/1977 |
| IT | 1150612 B | 12/1986 |
| WO | WO 00/11009 A2 | 3/2000 |

OTHER PUBLICATIONS

Kawaii, J. Agric. Food Chem. 1999, 47, 3565-3571. (Year: 1999).*
Internaitonal Search Report (Form PCT/ISA/210), dated Mar. 17, 2016, for International No. PCT/EP2016/052165.
Latif, Pharm. Anal. Acta. 2017, vol. 8, No. 8, pp. 1-4, 2017.
ThermoFisher Scientific, Residual Solvent Analysis Information, downloaded Dec. 28, 2018, https://www.thermofisher.com/us/en/home/industrial/pharma-biopharma/pharma-biopharma-learning-center/pharmaceutical-qa-qc-information/residual-solvent-analysis-information.html (Year 2018).
U.S. Notice of Allowance for U.S. Appl. No. 15/544,174, dated Jan. 3, 2019.
U.S. Restriction Requirement for U.S. Appl. No. 15/544,174, dated Aug. 3, 2018.

\* cited by examiner

*Primary Examiner* — Layla D Berry
(74) *Attorney, Agent, or Firm* — Birch, Stewart, Kolasch & Birch, LLP

(57) ABSTRACT

Provided is a process for the preparation of diosmin from hesperidin. The process involves the oxidation of acylated hesperidin with iodine or bromine in a $C_2$-$C_4$ carboxylic acid medium and subsequent treatment with an inorganic base to partially neutralize the acidic media. The process allows obtaining diosmin with low iodine or bromine content, avoiding the use of organic solvents.

11 Claims, No Drawings

PROCESS FOR THE PREPARATION OF DIOSMIN

CROSS REFERENCE TO RELATED APPLICATIONS

This application is a Continuation of copending application Ser. No. 15/544,174, filed on Jul. 17, 2017, which is a national phase of PCT International Application No. PCT/EP2016/052165 filed on Feb. 2, 2016, which claims priority under 35 U.S.C. § 119(a) to Patent Application No. 15153537.4, filed in Europe on Feb. 3, 2015, all of which are hereby expressly incorporated by reference into the present application.

TECHNICAL FIELD

The present invention relates to a process for the preparation of diosmin, which is a pharmacologically active flavonoid.

BACKGROUND ART

Diosmin is the International Non-proprietary Name assigned to the product 7-[[6-O-(6-Deoxy-α-L-mannopyranosyl)-β-D-gluocopyranosyl]oxy-5-hydroxy-2-(3-hydroxy-4-methoxyphenyl)-4H-1-benzopyran-4-one (CAS 520-27-4), which has the following chemical structure:

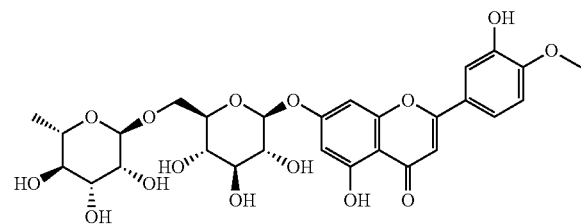

Diosmin is a naturally occurring flavonoid glycoside that can be obtained from various plant sources.

Diosmin is used in therapy due to its pharmacological activity as phlebotonic and vascular protecting agent, so it is indicated, for example, for the treatment of chronic venous insufficiency.

Industrially, diosmin is usually manufactured starting from the flavonoid hesperidin, which is widely available by extraction from citrus fruits.

Structurally, diosmin only differs from hesperidin in the double bond between carbon atoms 2-3 of the benzopyran-4-one central ring, so hesperidin has the following chemical structure:

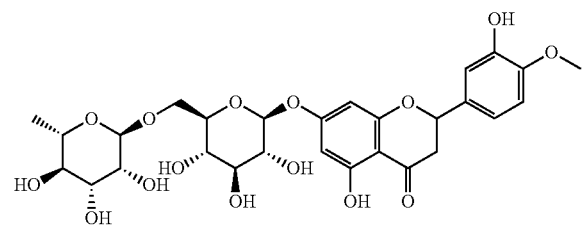

Therefore, for obtaining diosmin from hesperidin this single bond must be oxidized to a double bond.

In prior art, a number of processes have been disclosed to convert hesperidin into diosmin, that are suitable to be implemented industrially. Most of these processes are based on the use of halogens, namely iodine or bromine, for performing the oxidation step, typically using a halogenation/dehydrohalogenation mechanism to obtain the double bond.

Occasionally, the hydroxyl groups of hesperidin must be protected before performing the halogenation/dehydrohalogenation step.

One of the main difficulties faced in such processes is that special care has to be taken to eliminate iodinated or brominated intermediates or by-products formed during the process, so to obtain diosmin with an acceptable purity level as required, for example, in the European Pharmacopoeia, where the maximum allowed iodine content is 1000 ppm (0.1%).

In the processes disclosed so far, the elimination of iodine or bromine always requires basic conditions, either by treatment with hydroalcoholic alkaline solutions or, alternatively, with organic bases, such as morpholine or pyridine.

Thus, for example, in the German patent application DE2602314-A1 a process is disclosed for preparing diosmin wherein hesperidin is first acetylated using acetic anhydride, to protect the hydroxyl groups. The obtained acetylated hesperidin is isolated, and subsequently oxidized by treatment with bromine in a solvent such as ethyl acetate, ethylene chloride or acetic acid. The final dehydrobromination and deacetylation steps are performed in a hydroalcoholic alkaline solution, namely by treatment with a mixture of methanol and aqueous sodium hydroxide. The crude diosmin thus obtained is recrystallized, for example by dissolving it in a solution of sodium hydroxide in a mixture of water/methanol/pyridine, and subsequently acidifying with acetic acid to precipitate diosmin.

In the Spanish patent application ES440427 a process is disclosed wherein hesperidin is also first acetylated with acetic anhydride, using pyridine as catalyst, and subsequently it is brominated with N-bromosuccinimide in acetic acid and in the presence of bezoyl peroxide. The final dehydrobromination and deacetylation steps are also performed by treatment with a hydroalcoholic alkaline solution, using a mixture of ethanol and aqueous sodium hydroxide.

Alternatively, in the Italian patent IT1150612-B it is suggested the use of a phase transfer catalyst to achieve a complete dehydrobromination and deacetylation using milder conditions. Thus, according to this process, acetylated hesperidin is first brominated with bromine in 1,2-dichloroethane, and the following dehydrobromination and deacetylation step is performed in a biphasic system benzene/water or toluene/water using n-tetrabutylammonium sulfate as phase transfer catalyst.

Other processes disclosed in prior art, relate to the preparation of diosmin by halogenation/dehydrohalogenation of non-protected hesperidin, by performing the reaction in a weakly basic organic solvent, preferably pyridine, as described in the German patent DE2740950-A1.

Similarly, in the Belgian patent application BE904614-A1 it is disclosed that, as an alternative to the use of pyridine as solvent, hesperidin can be iodinated using an inert organic solvent, such as dimethylformamide or dimethylsulfoxide, but containing a certain amount of base to allow the elimination of iodine.

In the international patent application WO00/11009-A2 it is disclosed a process to obtain diosmin with low iodine content by reacting hesperidin with iodine in pyridine containing catalytic amounts of a mineral base, for example, sodium hydroxide, potassium hydroxide or calcium carbonate. The content of residual iodine can still be lowered by treatment of the final product with morpholine.

Therefore, despite the different alternatives proposed so far in the state of the art, the preparation of diosmin is still challenging, especially for obtaining it with low iodine and/or bromine content and using an economical and industrially-feasible process.

Particularly, in one way or another, all the proposed methods require the extensive use of different organic solvents, and thus, the obtained diosmin inevitably contains residual organic solvents, which is not desirable for its use as a drug. Moreover, the industrial use of organic solvents is always troublesome, since they involve high environmental impact and also potential occupational health hazards for the workers, apart from an increase in the manufacturing cost.

So, it would be desirable to develop an alternative method for manufacturing diosmin of high purity, especially with low iodine and/or bromine content, and avoiding the use of organic solvents.

OBJECT OF THE INVENTION

The object of the present invention is a process for the preparation of diosmin.

A second aspect of the invention relates to diosmin obtainable by such process.

DETAILED DESCRIPTION OF THE INVENTION

In a first aspect, the present invention relates to a process for the preparation of diosmin from hesperidin comprising the following steps:

a) acylating hesperidin with the anhydride of a $C_2$-$C_4$ carboxylic acid;
b) treating the mixture obtained in step a) with a halogen selected from iodine and bromine in aqueous medium;
c) treating the mixture obtained in step b) with an inorganic base to reach a pH value in the range 3.5-6.5;
d) deacylating the acylated diosmin obtained in step c) by treatment with an an inorganic base, in particular an aqueous solution of an inorganic base;

wherein no organic solvent is added throughout the process.

The authors of the present invention have developed a new process which, surprisingly, allows the manufacture of diosmin of improved purity, namely with low iodine and bromine content without the need to use organic solvents during the process.

The process according to the present invention relates to the preparation of diosmin from hesperidin. Hesperidin is the common name of the product (2S)-7-[[6-O-(6-deoxy-α-L-mannopyranosyl)-β-D-glucopyranosyl]oxy]-5-hydroxy-2-(3-hydroxy-4-methoxyphenyl)-2,3-dihydro-4H-1-benzopyran-4-one (CAS 520-26-3). Hesperidin is a product of natural origin, obtained from citrus fruits, and is commercially available from several sources.

The process involves first preparing an acylated derivative of hesperidin, which is subsequently oxidized by means of halogenation/dehydrohalogenation mechanism, to obtain the acylated diosmin, which is finally deacylated to render diosmin. The process is schematically represented in the following figure, though the depicted intermediates are preferably not isolated in the process:

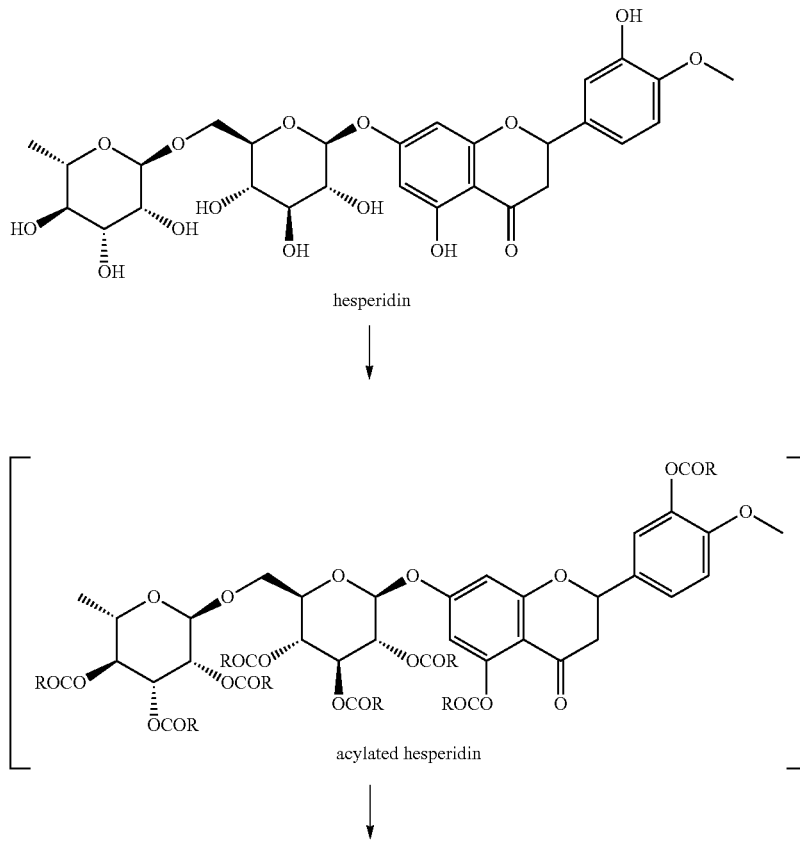

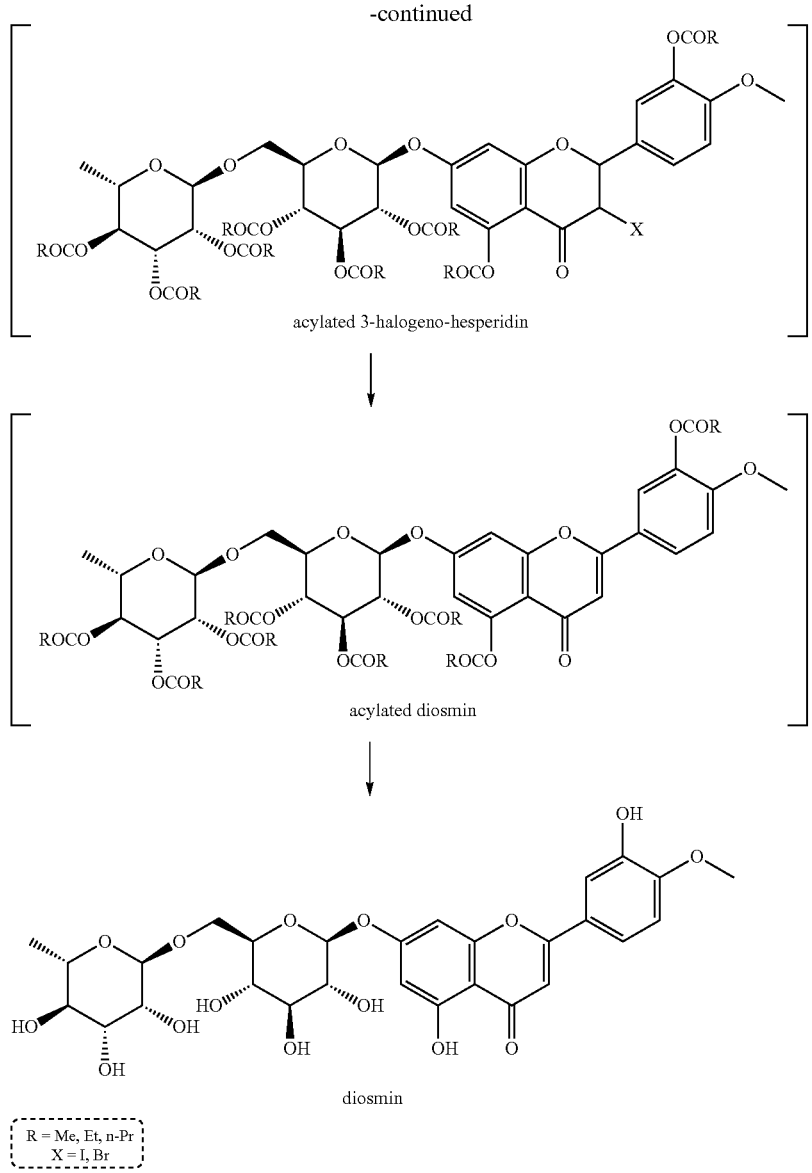

acylated 3-halogeno-hesperidin acylated diosmin diosmin

R = Me, Et, n-Pr
X = I, Br

In step a) of the process hesperidin is protected, i.e., its hydroxyl groups (OH) are converted into acyl groups (O—CO—$C_{1-3}$alkyl). To that end, hesperidin reacts with the anhydride of a $C_2$-$C_4$ carboxylic acid (in the following also called $C_2$-$C_4$ carboxylic acid anhydride) to obtain acylated hesperidin, and the corresponding $C_2$-$C_4$ carboxylic acid is released to the reaction media.

The $C_2$-$C_4$ carboxylic acid anhydride is the reactant used for acylating hesperidin, and it acts as well as the only solvent in this step. Preferably it is used in a stoichiometric amount, i.e. the molar ratio anhydride:hesperidin is about 8, so eight molecules of the $C_2$-$C_4$ carboxylic acid anhydride are needed for acylating the eight hydroxyl groups present in each hesperidin molecule, so substantially all $C_2$-$C_4$ carboxylic acid anhydride used is consumed in this step, to obtain acylated hesperidin and the $C_2$-$C_4$ carboxylic acid. If eventually a small amount of $C_2$-$C_4$ carboxylic acid anhydride remains unreacted, it is hydrolyzed to the $C_2$-$C_4$ carboxylic acid in aqueous subsequent stages.

Preferably, a catalyst is used for the acylation reaction of step a). The catalyst is preferably selected from sodium acetate and potassium acetate. More preferably, potassium acetate is used as catalyst.

The catalyst is preferably used in a molar ratio comprised between 0.1 and 1, relative to hesperidin.

The $C_2$-$C_4$ carboxylic acid anhydride is selected from acetic anhydride, propanoic anhydride, butanoic anhydride and mixtures thereof. In a preferred embodiment of the invention, acetic anhydride is used. According to this preferred embodiment, acetylated hesperidin is obtained, and acetic acid is released to the reaction media.

The reaction is carried out at a temperature preferably comprised between 90° C. and 150° C., more preferably comprised between 110° C. and 140° C.

The reaction is allowed to proceed under stirring for a time preferably comprised between 0.25 h and 6 h, more preferably comprised between 0.5 h and 3 h.

Next, the reaction mixture preferably is cooled to a temperature below 90° C., preferably comprised between 30° C. and 90° C.

In step b) of the process, the reaction mixture obtained in step a), without isolation of the acylated hesperidin, is directly treated with a halogen selected from iodine and bromine. The halogen reagent is preferably used in an aqueous medium, in particular in water as a solvent.

In this step, the acylated hesperidin is oxidized to acylated diosmin through a halogenation and dehydrohalogenation mechanism. Therefore, by reaction with molecular halogen ($X_2$), either molecular iodine ($I_2$) or molecular bromine ($Br_2$), a halogen atom is first added to the 3-position of acyl hesperidin, and subsequently a double bond is formed by releasing hydrogen halide (hydrogen iodide, HI, or hydrogen bromide, HBr), thus obtaining acylated diosmin.

According to one embodiment, the halogen used in step b) can be added in the form of molecular halogen ($X_2$). Preferably, the halogen is used in a stoichiometric amount.

According to another embodiment, a halogen precursor, namely an alkali metal halide or an alkaline earth metal halide, which is oxidized in the reaction medium by an oxidant, can be used so that the molecular halogen ($X_2$) is formed in situ. The halogen precursor can be added in a stoichiometric amount and the oxidant is used in a stoichiometric amount. The molecular halogen is then produced in situ in a stoichiometric amount.

According to another embodiment, the molecular halogen is used in a catalytic amount and an oxidant is used in a stoichiometric amount. In this embodiment the released hydrogen halide (via dehydrohalogenation of the acylated 3-halogenohesperidine) will again be oxidized to molecular halogen and reused in the reaction.

According to another embodiment, the halide is used in a catalytic amount and an oxidant is used in a stoichiometric amount. In this embodiment a catalytic amount of molecular halogen is produced in situ and the released hydrogen halide (via dehydrohalogenation of the acylated 3-halogenohesperidine) will again be oxidized to molecular halogen and reused in the reaction.

The expression "catalytic amount" as used herein means 0.01 to 0.2 mole, relative to the acylated hesperidine.

The expression "stoichiometric amount" as used herein means 0.8 to 1.2 mole, preferably 0.9 to 1.1 mole, relative to the acylated hesperidine.

When a halogen precursor is used, it is preferably selected from the group consisting of sodium iodide (NaI), potassium iodide (KI), calcium iodide ($CaI_2$), magnesium iodide ($MgI_2$), sodium bromide (NaBr), potassium bromide (KBr), calcium bromide ($CaBr_2$), magnesium bromide ($MgBr_2$), and mixtures thereof; more preferably is selected from sodium iodide, potassium iodide, sodium bromide and potassium bromide. The use of a halogen precursor has the advantage that the hydrogen halide which is released when forming the double bond may be re-oxidized by the oxidant to molecular halogen, which can be reused in the reaction.

In an embodiment of the invention, the halogen used in step b) is iodine ($I_2$). In a more preferred embodiment, a halogen precursor is used selected from, sodium iodide, potassium iodide, calcium iodide, magnesium iodide and mixtures thereof, preferably selected from sodium iodide, potassium iodide and mixtures thereof to form the iodine in situ.

In another embodiment of the invention, the halogen used in step b) is bromine ($Br_2$). In a more preferred embodiment, a halogen precursor is used is used selected from, sodium bromide, potassium bromide, calcium bromide, magnesium bromide, and mixtures thereof, preferably selected from sodium bromide, potassium bromide and mixtures thereof to form the bromine in situ.

The oxidant which may be used in step b) of the invention is preferably selected from the group consisting of hydrogen peroxide, sodium percarbonate, potassium percarbonate, sodium perborate, potassium perborate, sodium permanganate, potassium permanganate, sodium dichromate, potassium dichromate, and hydrates thereof. Thus, for example, potassium percarbonate is usually available as monohydrate ($K_2C_2O_6H_2O$); sodium perborate is usually available in hydrated form, either monohydrate ($NaBO_3H_2O$), trihydrate ($NaBO_3 \cdot 3H_2O$) or tetrahydrate ($NaBO_3 \cdot 4H_2O$); potassium perborate is usually available in monohydrate form ($2KBO_3 \cdot H_2O$); sodium permanganate is usually available in hydrated form, either monohydrate ($NaMnO_4 \cdot H_2O$) or trihydrate ($NaMnO_4 \cdot 3H_2O$); and sodium dichromate is usually available as a dihydrate ($Na_2Cr_2O_7 \cdot 2H_2O$); so all of them are suitable oxidant hydrated forms for step b). Sodium percarbonate ($Na_2CO_3 \cdot 3/2H_2O_2$), is an adduct of sodium carbonate and hydrogen peroxide.

The oxidant is preferably used in 1-1.5 molar equivalent amount relative to acylated hesperidin.

In a preferred embodiment of the invention, the oxidant of step b) is hydrogen peroxide.

When the oxidant is hydrogen peroxide, it is preferably added as an aqueous solution, more preferably having a concentration in the range 3-50%, more preferably in the range 4-30%, wherein the percentages are by weight (w/w).

In another preferred embodiment of the invention, the oxidant of step b) is selected from sodium percarbonate, potassium percarbonate, sodium perborate, potassium perborate, and hydrates thereof, preferably selected from sodium perborate, potassium perborate and hydrates thereof, more preferably the oxidant is sodium perborate or hydrates thereof.

Preferably, a strong mineral acid is also added in step b), together with the oxidant and the halogen. The strong mineral acid is preferably selected from hydrochloric acid, nitric acid or sulphuric acid. Sulphuric acid is preferred. The strong mineral acid is preferably used in a molar ratio in the range 0.001-0.01 relative to acylated hesperidin.

The reaction of step b) is preferably carried out at reflux conditions.

In step c) of the process, the reaction mixture obtained in step b) is treated with an inorganic base to reach a pH value in the range 3.5-6.5. The inorganic base can be added to the aqueous reaction mixture in solid form or as an aqueous solution.

The inorganic base in step c) is preferably selected from an alkali hydroxide, an alkaline earth hydroxide, an alkali carbonate, an alkaline earth carbonate, an alkali bicarbonate and an alkaline earth bicarbonate, preferably selected from the group consisting of sodium hydroxide, potassium hydroxide, calcium hydroxide, magnesium hydroxide, sodium carbonate, potassium carbonate, calcium carbonate, magnesium carbonate, hydrates thereof, and mixtures thereof.

In an embodiment of the invention, the inorganic base of step c) is selected from the group consisting of sodium hydroxide, potassium hydroxide, calcium hydroxide, magnesium hydroxide, and mixtures thereof, preferably selected from sodium hydroxide, potassium hydroxide and mixtures thereof, and more preferably is potassium hydroxide.

In another embodiment of the invention, the inorganic base of step c) is selected from the group consisting of sodium carbonate, potassium carbonate, calcium carbonate, magnesium carbonate, hydrates thereof, and mixtures thereof, preferably selected from sodium carbonate, potassium carbonate, hydrates thereof and mixtures thereof, more preferably is sodium carbonate or hydrates thereof.

In step c), the strongly acidic medium of the reaction mixture obtained in step b) is partially neutralized, until reaching a pH comprised between 3.5 and 6.5, preferably comprised between 4.0 and 6.0, and still more preferably comprised between 4.5 and 5.5.

This treatment is carried out at a temperature preferably comprised between 90° C. and 125° C., more preferably comprised between 100° C. and 120° C., for a time preferably comprised between 0.5 and 10 hours, more preferably comprised between 1 and 8 hours.

It was found that by using this treatment with an inorganic base after the oxidation step b), until reaching the specified pH value, the acylated diosmin obtained at this stage of the process had very low halogen content, either bromine or iodine, depending on the halogen used in the oxidation step b), namely less than 1000 ppm. In this way, the process of the present invention provides an effective dehalogenation, either debromination or deiodination, of diosmin still in acidic conditions.

This fact was surprising, since in the prior art, it is disclosed that to achieve a complete dehydrohalogenation and for the reduction of the iodine or bromine content to an acceptable level it is necessary to have basic conditions, either by treatment with an hydroalcoholic alkaline solution or with organic basic solvents, such as morpholine or pyridine.

The method of the present invention avoids these subsequent alkaline treatments involving the use of organic solvents.

Step c) of the present process, involving the treatment with an inorganic base until reaching the specified pH value, is considered key to achieve a complete dehalogenation of acylated diosmin.

Indeed, it was found that after step b) the iodine or bromine content of the obtained acylated diosmin is about 5%, which is unacceptably high, and is the result of remaining halogenated intermediates and/or halogenated by-products.

Surprisingly, after step c) acylated diosmin has iodine or bromine content of less than 0.1%.

The halogen content is determined by a potentiometry assay after oxygen combustion, according to the methods 2.2.36 (Potentiometric determination of ionic concentration using ion-selective electrodes) and 2.5.10 (Oxygen-flask method) disclosed in the European Pharmacopoeia 8.3 Edition.

Finally, in step d) acylated diosmin is deacylated by treatment with aqueous inorganic base.

The inorganic base in step d) can be used in solid form or as an aqueous solution. The inorganic base is preferably selected from an alkali hydroxide, an alkaline earth hydroxide, an alkali carbonate, an alkaline earth carbonate, an alkali bicarbonate and an alkaline earth bicarbonate, preferably selected from the group consisting of sodium hydroxide, potassium hydroxide, calcium hydroxide, magnesium hydroxide, sodium carbonate, potassium carbonate, calcium carbonate, magnesium carbonate, hydrates thereof, and mixtures thereof; more preferably selected from the group consisting of sodium hydroxide, potassium hydroxide, calcium hydroxide, magnesium hydroxide and mixtures thereof, still more preferably selected from sodium hydroxide and potassium hydroxide and mixtures thereof, and still more preferably is sodium hydroxide.

After the addition of the inorganic base in step d), the pH of the reaction medium is preferably greater than 11, more preferably greater than 12, and still more preferably greater than 13.

Diosmin can be subsequently isolated by adding a mineral acid to the reaction medium, so diosmin is precipitated and can be recovered by filtration. The mineral acid is preferably sulphuric acid. The pH of the reaction medium after the addition of the mineral acid is preferably comprised between 6.5 and 8.5, more preferably comprised between 7.0 and 8.0.

All the particular embodiments and preferred options disclosed above for each of the steps a), b), c) and d) of the process can be independently combined with all the particular embodiments and preferred options of the other steps. Therefore, the present invention includes all possible combinations of the particular embodiments and preferred options described above for each of those steps.

In a preferred embodiment, the present invention relates to a process for the preparation of diosmin from hesperidin comprising the following steps:
  a) acylating hesperidin with a $C_2$-$C_4$ carboxylic acid anhydride, preferably with acetic anhydride;
  b) treating the mixture obtained in step a) with hydrogen peroxide and a iodine compound (in particular in catalytic amounts) selected from molecular iodine ($I_2$), sodium iodide, potassium iodide, calcium iodide, magnesium iodide and mixtures thereof, preferably selected from sodium iodide, potassium iodide and mixtures thereof, and more preferably sodium iodide;
  c) treating the mixture obtained in step b) with an inorganic base selected from sodium hydroxide, potassium hydroxide, calcium hydroxide, magnesium hydroxide and mixtures thereof, preferably selected from sodium hydroxide, potassium hydroxide and mixtures thereof, more preferably potassium hydroxide, to reach a pH value in the range 3.5-6.5, preferably in the range 4.0-6.0, more preferably in the range 4.5-5.5;
  d) deacylating the acylated diosmin obtained in step c) by treatment with an inorganic base, preferably with an aqueous solution of an inorganic base, selected from sodium hydroxide, potassium hydroxide, calcium hydroxide and magnesium hydroxide, preferably selected from sodium hydroxide and potassium hydroxide;
  wherein no organic solvent is added throughout the process.

In another preferred embodiment, the present invention relates to a process for the preparation of diosmin from hesperidin comprising the following steps:
  a) acylating hesperidin with a $C_2$-$C_4$ carboxylic acid anhydride, preferably with acetic anhydride;
  b) treating the mixture obtained in step a) with hydrogen peroxide and a bromine compound (in particular in catalytic amounts) selected from molecular bromine ($Br_2$), sodium bromide, potassium bromide, calcium bromide, magnesium bromide, and mixtures thereof, preferably selected from sodium bromide, potassium bromide and mixtures thereof;
  c) treating the mixture obtained in step b) with an inorganic base selected from sodium hydroxide, potassium hydroxide, calcium hydroxide, magnesium hydroxide and mixtures thereof, preferably selected from sodium hydroxide, potassium hydroxide and mixtures thereof, more preferably potassium hydroxide, to reach a pH value in the range 3.5-6.5, preferably in the range 4.0-6.0, more preferably in the range 4.5-5.5;

d) deacylating the acylated diosmin obtained in step c) by treatment with an inorganic base, preferably an aqueous solution of an inorganic base, selected from sodium hydroxide, potassium hydroxide, calcium hydroxide and magnesium hydroxide, preferably selected from sodium hydroxide and potassium hydroxide;

wherein no organic solvent is added throughout the process.

In another preferred embodiment, the present invention relates to a process for the preparation of diosmin from hesperidin comprising the following steps:
a) acylating hesperidin with a $C_2$-$C_4$ carboxylic acid anhydride, preferably with acetic anhydride;
b) treating the mixture obtained in step a) with an oxidant selected from sodium percarbonate, potassium percarbonate, sodium perborate, potassium perborate, and hydrates thereof, preferably selected from sodium perborate, potassium perborate and hydrates thereof, more preferably the oxidant is sodium perborate or hydrates thereof, and a iodine compound (in particular in catalytic amounts) selected from molecular iodine ($I_2$), sodium iodide, potassium iodide, calcium iodide, magnesium iodide and mixtures thereof, preferably selected from sodium iodide, potassium iodide and mixtures thereof, and more preferably sodium iodide;
c) treating the mixture obtained in step b) with an inorganic base selected from sodium hydroxide, potassium hydroxide, calcium hydroxide, magnesium hydroxide and mixtures thereof, preferably selected from sodium hydroxide, potassium hydroxide and mixtures thereof, more preferably potassium hydroxide, to reach a pH value in the range 3.5-6.5, preferably in the range 4.0-6.0, more preferably in the range 4.5-5.5;
d) deacylating the acylated diosmin obtained in step c) by treatment with an inorganic base, preferably an aqueous solution of an inorganic base, selected from sodium hydroxide, potassium hydroxide, calcium hydroxide and magnesium hydroxide, preferably selected from sodium hydroxide and potassium hydroxide;

wherein no organic solvent is added throughout the process.

In another preferred embodiment, the present invention relates to a process for the preparation of diosmin from hesperidin comprising the following steps:
a) acylating hesperidin with a $C_2$-$C_4$ carboxylic acid anhydride, preferably with acetic anhydride;
b) treating the mixture obtained in step a) with an oxidant selected from sodium percarbonate, potassium percarbonate, sodium perborate, potassium perborate, and hydrates thereof, preferably selected from sodium perborate, potassium perborate and hydrates thereof, more preferably the oxidant is sodium perborate or hydrates thereof, and a bromine compound (in particular in catalytic amounts) selected from molecular bromine ($Br_2$), sodium bromide, potassium bromide, calcium bromide, magnesium bromide, and mixtures thereof, preferably selected from sodium bromide, potassium bromide and mixtures thereof;
c) treating the mixture obtained in step b) with an inorganic base selected from sodium hydroxide, potassium hydroxide, calcium hydroxide, magnesium hydroxide and mixtures thereof, preferably selected from sodium hydroxide, potassium hydroxide and mixtures thereof, more preferably potassium hydroxide, to reach a pH value in the range 3.5-6.5, preferably in the range 4.0-6.0, more preferably in the range 4.5-5.5;

d) deacylating the acylated diosmin obtained in step c) by treatment with an inorganic base, preferably an aqueous solution of an inorganic base, selected from sodium hydroxide, potassium hydroxide, calcium hydroxide and magnesium hydroxide, preferably selected from sodium hydroxide and potassium hydroxide;

wherein no organic solvent is added throughout the process.

In a preferred embodiment, the present invention relates to a process for the preparation of diosmin from hesperidin comprising the following steps:
a) acylating hesperidin with a $C_2$-$C_4$ carboxylic acid anhydride, preferably with acetic anhydride;
b) treating the mixture obtained in step a) with hydrogen peroxide and a iodine compound (in particular in catalytic amounts) selected from molecular iodine ($I_2$), sodium iodide, potassium iodide, calcium iodide, magnesium iodide and mixtures thereof, preferably selected from sodium iodide, potassium iodide and mixtures thereof, and more preferably sodium iodide;
c) treating the mixture obtained in step b) with an inorganic base selected from sodium carbonate, potassium carbonate, calcium carbonate, magnesium carbonate, hydrates thereof and mixtures thereof, preferably selected from sodium carbonate, potassium carbonate, hydrates thereof and mixtures thereof, more preferably with sodium carbonate or hydrates thereof, to reach a pH value in the range 3.5-6.5, preferably in the range 4.0-6.0, more preferably in the range 4.5-5.5;
d) deacylating the acylated diosmin obtained in step c) by treatment with an inorganic base, preferably an aqueous solution of an inorganic base, selected from sodium hydroxide, potassium hydroxide, calcium hydroxide, and magnesium hydroxide, preferably selected from sodium hydroxide and potassium hydroxide;

wherein no organic solvent is added throughout the process.

In another preferred embodiment, the present invention relates to a process for the preparation of diosmin from hesperidin comprising the following steps:
a) acylating hesperidin with a $C_2$-$C_4$ carboxylic acid anhydride, preferably with acetic anhydride;
b) treating the mixture obtained in step a) with hydrogen peroxide and a bromine compound (in particular in catalytic amounts) selected from molecular bromine ($Br_2$), sodium bromide, potassium bromide, calcium bromide, magnesium bromide, and mixtures thereof, preferably selected from sodium bromide, potassium bromide and mixtures thereof;
c) treating the mixture obtained in step b) with an inorganic base selected from sodium carbonate, potassium carbonate, calcium carbonate, magnesium carbonate, hydrates thereof and mixtures thereof, preferably selected from sodium carbonate, potassium carbonate, hydrates thereof and mixtures thereof, more preferably with sodium carbonate or hydrates thereof, to reach a pH value in the range 3.5-6.5, preferably in the range 4.0-6.0, more preferably in the range 4.5-5.5;
d) deacylating the acylated diosmin obtained in step c) by treatment with an inorganic base, preferably an aqueous solution of an inorganic base, selected from sodium hydroxide, potassium hydroxide, calcium hydroxide and magnesium hydroxide, preferably selected from sodium hydroxide and potassium hydroxide;

wherein no organic solvent is added throughout the process.

In another preferred embodiment, the present invention relates to a process for the preparation of diosmin from hesperidin comprising the following steps:
a) acylating hesperidin with a $C_2$-$C_4$ carboxylic acid anhydride, preferably with acetic anhydride;
b) treating the mixture obtained in step a) with an oxidant selected from sodium percarbonate, potassium percarbonate, sodium perborate, potassium perborate, and hydrates thereof, preferably selected from sodium perborate, potassium perborate and hydrates thereof, more preferably the oxidant is sodium perborate or hydrates thereof, and a iodine compound (in particular in catalytic amounts) selected from molecular iodine ($I_2$), sodium iodide, potassium iodide, calcium iodide, magnesium iodide and mixtures thereof, preferably selected from sodium iodide, potassium iodide and mixtures thereof, and more preferably sodium iodide;
c) treating the mixture obtained in step b) with an inorganic base selected from sodium carbonate, potassium carbonate, calcium carbonate, magnesium carbonate, hydrates thereof and mixtures thereof, preferably selected from sodium carbonate, potassium carbonate, hydrates thereof and mixtures thereof, more preferably with sodium carbonate or hydrates thereof, to reach a pH value in the range 3.5-6.5, preferably in the range 4.0-6.0, more preferably in the range 4.5-5.5;
d) deacylating the acylated diosmin obtained in step c) by treatment with an inorganic base, preferably an aqueous solution of an inorganic base, selected from sodium hydroxide, potassium hydroxide, calcium hydroxide and magnesium hydroxide, preferably selected from sodium hydroxide and potassium hydroxide;
wherein no organic solvent is added throughout the process.

In another preferred embodiment, the present invention relates to a process for the preparation of diosmin from hesperidin comprising the following steps:
a) acylating hesperidin with a $C_2$-$C_4$ carboxylic acid anhydride, preferably with acetic anhydride;
b) treating the mixture obtained in step a) with an oxidant selected from sodium percarbonate, potassium percarbonate, sodium perborate, potassium perborate, and hydrates thereof, preferably selected from sodium perborate, potassium perborate and hydrates thereof, more preferably the oxidant is sodium perborate or hydrates thereof, and a bromine compound (in particular in catalytic amounts) selected from molecular bromine ($Br_2$), sodium bromide, potassium bromide, calcium bromide, magnesium bromide, and mixtures thereof, preferably selected from sodium bromide, potassium bromide and mixtures thereof;
c) treating the mixture obtained in step b) with an inorganic base selected from sodium carbonate, potassium carbonate, calcium carbonate, magnesium carbonate, hydrates thereof and mixtures thereof, preferably selected from sodium carbonate, potassium carbonate, hydrates thereof and mixtures thereof, more preferably with sodium carbonate or hydrates thereof, to reach a pH value in the range 3.5-6.5, preferably in the range 4.0-6.0, more preferably in the range 4.5-5.5;
d) deacylating the acylated diosmin obtained in step c) by treatment with an inorganic base, preferably an aqueous solution of an inorganic base, selected from sodium hydroxide, potassium hydroxide, calcium hydroxide and magnesium hydroxide, preferably selected from sodium hydroxide and potassium hydroxide;
wherein no organic solvent is added throughout the process.

Optionally, diosmin obtained after step d) may be subsequently purified by one or more crystallizations in aqueous media.

For example, diosmin can be recrystallized in an alkaline solution comprising water/alkali hydroxide/sulphuric acid, by seeding diosmin. The alkali hydroxide is for example sodium hydroxide or potassium hydroxide.

Alternatively, or additionally, diosmin can be recrystallized by dissolving it in aqueous alkali hydroxide alkaline solution, and subsequently acidifying with sulphuric acid to precipitate diosmin. The alkali hydroxide is for example sodium hydroxide or potassium hydroxide.

The present method is industrially advantageous since it avoids the use of organic solvents throughout the process.

Avoiding the use of organic solvents in chemical manufacturing plants has several advantages. Firstly, the environmental impact of the process is reduced by avoiding the discharge of the solvents into the process waters and their emission as volatile organic compounds (VOCs). Also, it reduces the potential occupational hazards to the workers. And furthermore, it considerably reduces the production costs.

On the other hand, the process of the present invention provides, for the first time, diosmin with halogen content of less than 1000 ppm and free from residual organic solvents. The halogen content means bromine content in the case that bromine has been used in step b) of the process, or either means iodine in the case that iodine has been used in step b) of the process.

The only organic solvent used in the current method is the $C_2$-$C_4$ carboxylic acid anhydride used in step a), which is at the same time a reactant of the process, so it is completely hydrolyzed to the corresponding $C_2$-$C_4$ carboxylic acid, while the $C_2$-$C_4$ carboxylic acid released is in turn completely removed through the process waters in the form of alkali or alkaline earth salts formed with the alkali or alkaline earth bases, which are used in excess in steps c) and d) of the process.

So, with the present method, diosmin is industrially obtained free from organic solvents.

Particularly, diosmin obtained by the present method is free from alcohol solvents (such as butanol, propanol, ethanol or methanol), amine solvents (such as pyridine or morpholine), aromatic solvents (such as toluene), amide solvents (such as dimethylformamide), sulphur-containing organic solvents (such as dimethyl sulfoxide), or halogenated solvents (such as chloroform, ethylene chloride or dichloromethane).

Therefore another aspect of the present invention is diosmin obtainable by this process.

In a preferred embodiment, this aspect of the invention relates to diosmin obtainable by this process, characterized in that it has halogen content of less than 1000 ppm, and is free from residual organic solvents.

In a particular embodiment, it relates to diosmin obtainable by this process, characterized in that it has iodine content of less than 1000 ppm, and is free from residual organic solvents, in the case that iodine has been used in step b) of the process.

In another particular embodiment, it relates to diosmin obtainable by this process, characterized in that it has bromine content of less than 1000 ppm, and is free from residual organic solvents, in the case that bromine has been used in step b) of the process.

The halogen (iodine or bromine) content is determined by a potentiometry assay after oxygen combustion, according to the methods 2.2.36 (Potentiometric determination of ionic concentration using ion-selective electrodes) and 2.5.10 (Oxygen-flask method) disclosed in the European Pharmacopoeia 8.3 Edition.

The following example is provided by way of illustration and should not be construed as limiting the present invention.

EXAMPLES

Example 1

160 g of acetic anhydride, 3 g of potassium acetate and 120 g of hesperidin are added to a reactor. The reaction medium is then heated to 115-120° C., maintaining this temperature for one hour approximately, and the medium is then cooled down to 60-70° C.

A sodium iodide solution in water (3.5 g, 24 mL) is added to the reaction vessel, and it is heated to reflux. Then, a solution made with 140 mL of 5.4% (w/w) aqueous hydrogen peroxide and 70 µL of sulphuric acid 7.5 N is added to the reactor, maintaining the reflux conditions. Afterwards, the reaction medium is refrigerated to 40-50° C. Subsequently, KOH (40 g) is added to the reaction mixture to maintain the pH in the range 3.5-5.5, the mixture heated to 115-120° C. for a minimum of 3 hours, and then cooled to 30° C.

The reaction mixture is added to a vessel containing aqueous NaOH solution (1200 mL, 2.0-2.5 M) and the mixture is kept for 90 minutes, and then sulphuric acid is added until reaching a pH of 7.5. The precipitate is then filtered and washed with water, to obtain wet crude diosmin.

The crude diosmin thus obtained is crystallized by dissolving it in aqueous NaOH solution, and subsequently acidifying with sulphuric acid until product precipitation.

The solid is filtered, washed with water and dried. 92 g of diosmin were obtained (77% yield). Purity 90% HPLC.

The iodine content was 750 ppm as determined by a potentiometry assay after oxygen combustion, according to the methods 2.2.36 (Potentiometric determination of ionic concentration using ion-selective electrodes) and 2.5.10 (Oxygen-flask method) disclosed in the European Pharmacopoeia 8.3 Edition.

The invention claimed is:

1. Diosmin, or a pharmaceutically acceptable salt thereof, having a halogen content of more than 0 ppm to less than 1000 ppm and free from residual organic solvents.

2. The diosmin or pharmaceutically acceptable salt thereof according to claim 1, wherein the halogen content is more than 0 ppm to 750 ppm or less.

3. Diosmin, or a pharmaceutically acceptable salt thereof, comprising more than 0 ppm to less than 1000 ppm combined iodine and bromine and free from residual organic solvents.

4. The diosmin or pharmaceutically acceptable salt thereof according to claim 3, wherein the iodine content is more than 0 ppm to 750 ppm or less.

5. Diosmin, or a pharmaceutically acceptable salt thereof, having a halogen content of more than 0 ppm and free from residual organic solvents.

6. The diosmin or pharmaceutically acceptable salt thereof according to claim 1, wherein the diosmin or the pharmaceutically acceptable salt thereof is synthetic and obtained from hesperidin.

7. The diosmin or pharmaceutically acceptable salt thereof according to claim 3, wherein the diosmin or the pharmaceutically acceptable salt thereof is synthetic and obtained from hesperidin.

8. The diosmin or pharmaceutically acceptable salt thereof according to claim 5, wherein the diosmin or the pharmaceutically acceptable salt thereof is synthetic and obtained from hesperidin.

9. A composition comprising diosmin, or a pharmaceutically acceptable salt thereof, having a halogen content of more than 0 ppm to less than 1000 ppm and free from residual organic solvents.

10. A method of treating chronic venous insufficiency in a patient, comprising:
   administering, to said patient, an effective amount for treating chronic venous insufficiency of diosmin or a pharmaceutically acceptable salt thereof, having a halogen content of less than 1000 ppm and free from residual organic solvents,
   wherein the diosmin or the pharmaceutically acceptable salt thereof is obtained from hesperidin.

11. A pharmaceutically acceptable salt of diosmin, having a halogen content of more than 0 ppm to less than 1000 ppm and free from residual organic solvents.

* * * * *